United States Patent
Ulrich

(10) Patent No.: US 6,924,305 B2
(45) Date of Patent: Aug. 2, 2005

(54) DIAZOCINE DERIVATIVES AND THEIR USE AS TRYPTASE INHIBITORS

(75) Inventor: Wolf-Rüdiger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/466,906

(22) PCT Filed: Jan. 26, 2002

(86) PCT No.: PCT/EP02/00831

§ 371 (c)(1),
(2), (4) Date: Jul. 22, 2003

(87) PCT Pub. No.: WO02/060895

PCT Pub. Date: Aug. 8, 2002

(65) Prior Publication Data

US 2004/0072762 A1 Apr. 15, 2004

(30) Foreign Application Priority Data

Jan. 31, 2001 (EP) .............................. 01102098

(51) Int. Cl.[7] .................... C07D 403/14; A61K 31/395; A61P 43/00
(52) U.S. Cl. ...................................... 514/422; 540/460
(58) Field of Search ........................... 514/422; 540/460

(56) References Cited

U.S. PATENT DOCUMENTS 6,489,327 B1   12/2002   Bär et al.

FOREIGN PATENT DOCUMENTS

| WO | WO 95/32945 | 12/1995 |
|----|-------------|---------|
| WO | WO 96/09297 | 3/1996 |
| WO | WO 98/04537 | 2/1998 |
| WO | WO 99/12918 | 3/1999 |
| WO | WO 99/24395 | 5/1999 |
| WO | WO 99/24407 | 5/1999 |
| WO | WO 99/40073 | 8/1999 |
| WO | WO 99/40083 | 8/1999 |
| WO | WO 00/14097 | 3/2000 |
| WO | WO 01/10845 | 2/2001 |
| WO | WO 01/10848 | 2/2001 |
| WO | WO 01/19809 | 3/2001 |
| WO | WO 01/46128 | 6/2001 |
| WO | WO 01/46168 | 6/2001 |

Primary Examiner—Bruck Kifle
(74) Attorney, Agent, or Firm—Nath & Associates PLLC; Joshua B. Goldberg; Sheldon M. McGee

(57) ABSTRACT

Compounds of the formula I, in which B1, B2, R1, R2, R6, R7, K1 and K2 are as defined in the description are novel effective tryp-tase inhibitors.

7 Claims, No Drawings

DIAZOCINE DERIVATIVES AND THEIR USE AS TRYPTASE INHIBITORS

FIELD OF APPLICATION OF THE INVENTION

The invention relates to novel tryptase inhibitors which are used in the pharmaceutical industry for preparing medicaments.

KNOWN TECHNICAL BACKGROUND

The international applications WO95/32945, WO96/09297, WO98/04537, WO99/12918, WO99/24395, WO99/24407, WO99140073, WO99/40083 and WO00/14097 describe low-molecular-weight bivalent compounds for use as tryptase inhibitors.

DESCRIPTION OF THE INVENTION

It has now been found that the compounds of the formula I, which are described in more detail below, have surprising and particularly advantageous properties.

The invention provides compounds of the formula I

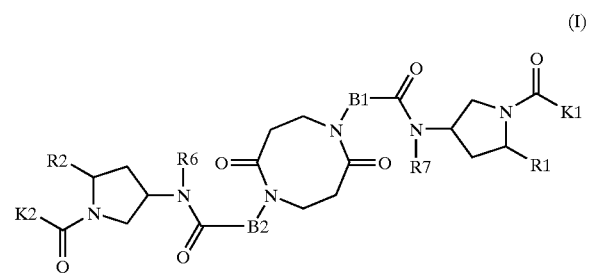

(I)

in which
K1 is —B3-Z1-B5-X1,
K2 is —B4-Z2-B6-X2,
B1 and B2 are identical or different and are 1–4C-alkylene,
B3 and B4 are identical or different and are a bond or 1–2C-alkylene,
B5 and B6 are identical or different and are a bond or 1–2C-alkylene,
X1 and X2 are Identical or different and are amino, aminocarbonyl, amidino or guanidino,
Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene,
R1 and R2 are identical or different and are C(O)OR3 or C(O)N(R4)R5,
R3 is hydrogen, 1–4C-alkyl, 3–7C-cycloalkyl, 3–7C-cycloalkylmethyl or benzyl,
R4 and R5 independently of one another are hydrogen, 1–4C-alkyl, 3–7C-cycloalkyl or 3–7C-cycloalkylmethyl, or R4 and R5 together, including the nitrogen atom to which they are attached, are a 1-pyrrolidinyl, 1-piperidinyl, 1-hexahydroazepinyl, 1-piperazinyl or 4-morpholinyl radical, R6 and R7 are identical or different and are hydrogen or 1–2C-alkyl, and the salts of these compounds.

1–4C-Alkyl denotes straight-chain or branched alkyl radicals having 1 to 4 carbon atoms. Examples which may be mentioned are the butyl, isobutyl, sec-butyl, tert-butyl, propyl, isopropyl, ethyl and the methyl radical.

3–7C-Cycloalkyl denotes cyclopropyl, cyclobutyl, cyclopentyl, cyclohexyl or cycloheptyl.

3–7C-Cycloalkylmethyl denotes a methyl radical which is substituted by one of the 3–7C-cycloalkyl radicals mentioned above. The 3–5C-cycloalkylmethyl radicals cyclopropylmethyl, cyclobutylmethyl and cyclopentylmethyl may be mentioned as being preferred.

1–4C-Alkylene denotes straight-chain or branched 1–4C-alkylene radicals, for example the methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—], 1,2-dimethylethylene [—CH(CH$_3$)—CH (CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—] or the 1-methylethylene [—CH(CH$_3$)—CH$_2$—] radical.

By definition, the groups Z1 and Z2 are located between groups B3 and B5 (—B3-Z1-B5—) and B4 and B6 (—B4-Z2-B6—), respectively. Accordingly, in the divalent groupings mentioned by way of example (for example 3,6-indolylene), the first number indicates the point of attachment to the group B3 and B4, respectively, and the second number indicates the point of attachment to the group B5 and B6, respectively.

The groups Z1 and Z2 can, inter alia, have the meanings 1,4-cyclohexylene and 1,3-cyclohexylene. The invention includes all compounds of the formula I in which the groups B3, B5 and B4, B6, respectively, are attached to the cyclohexylene radical (1e,4e), (1a,4a), (1e,4a), (1a,4e), (1e,3e), 1a,3a), (1e,3a) or (1a,3e). In this context, particular preference is given to the (1e,4e) attachment ("e" denotes equatorial and "a" denotes axial).

The substituted pyrrolidine building blocks of the compounds of the formula I may have various configurations. According to the Cahn, Ingold and Prelog nomenclature, these are referred to as (2S, 4S), (2R, 4R), (2S, 4R) and (2R, 4S). The invention includes compounds of the formula I having pyrrolidine building blocks of any of these configurations. Preference is given to those compounds of the formula I in which the configuration on the two pyrrolidine building blocks is (2S, 4S).

Suitable salts for compounds of the formula I are all acid addition salts. Particular mention may be made of the pharmaceutically acceptable salts of inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is confirmed and depending on which salt is desired—in an equimolar quantitative ratio or one differing therefrom.

Pharmacologically unacceptable salts which can be obtained initially as process products, for example in the preparation of the compounds according to the invention on an industrial scale, are converted into pharmacologically acceptable salts by processes known to the person skilled in the art.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Compounds of the formula I which are to be emphasized are those in which
K1 is —B3-Z1-B5-X1,
K2 is —B4-Z2-B6-X2,
B1 and B2 are identical or different and are 1–2C-alkylene,
B3 and B4 are identical or different and are a bond or 1–2C-alkylene,
B5 and B6 are identical or different and are a bond or 1–2C-alkylene,
X1 and X2 are identical or different and are amino or amidino,
Z1 and Z2 are identical or different and are 1,3-phenylene, 1,4-phenylene, 1,3-cyclohexylene or 1,4-cyclohexylene,
R1 and R2 are identical or different and are C(O)OR3 or C(O)N(R4)R5,
R3 is hydrogen, 1–4C-alkyl, 3–7C-cycloalkyl, 3–7C-cycloalkylmethyl or benzyl,
R4 and R5 independently of one another are hydrogen, 1–4C-alkyl, 3–7C-cycloalkyl or 3–7C-cycloalkylmethyl or R4 and R5 together; Including the nitrogen atom to which they are attached, are a 1-pyrrolidinyl, 1-piperidinyl, 1-hexahydroazepinyl, 1-piperazinyl or 4-morpholinyl radical,
R6 and R7 are identical or different and are hydrogen or 1–2C-alkyl, and the salts of these compounds.

Compounds of the formula I which are to be particularly emphasized are those in which
K1 is —B3-Z1-B5-X1,
K2 is —B4-Z2-B6-X2,
B1 and B2 are identical or different and are 1–2C-alkylene,
B3 and B4 are identical or different and are a bond or 1–2C-alkylene,
B5 and B6 are Identical or different and are a bond or 1–2C-alkylene,
X1 and X2 are identical or different and are amino or amidino,
Z1 and Z are identical or different and are 1,3-phenylene, 1,4-phenylene, 1,3-cyclohexylene or 1,4-cyclohexylene,
R1 and R2 are Identical or different and are C(O)OR3 or C(O)N(R4)R5,
R3 is hydrogen, 1–4C-alkyl, 3–7C-cycloalkyl, 3–7C-cycloalkylmethyl or benzyl,
R4 and R5 independently of one another are hydrogen, 1–4C-alkyl or 3–7C-cycloalkyl,
R6 and R7 are identical and are hydrogen, and the salts of these compounds.

Preferred compounds of the formula I are those in which
K1 is —B3-Z1-B5-X1,
K2 is —B4-Z2-B6-X2,
B1 and B2 are identical and are methylene,
B3 and B4 are identical and are a bond or ethylene,
B5 and B6 are identical and are methylene,
X1 and X2 are identical and are amino,
Z1 and Z2 are identical and are 1,4-phenylene or 1,4-cyclohexylene,
R1 and R2 are identical and are C(O)OR3 or C(O)N(R4)R5,
R3 is hydrogen, 1–4C-alkyl or benzyl,
R4 is hydrogen,
R5 is hydrogen or cyclopropyl,
R6 and R7 are identical and are hydrogen, and the salts of these compounds.

The synthesis of some exemplary compounds of the formula I is shown in reaction schemes 1 and 2 below. Further compounds of the formula 1, the preparation of which is not explicitly described in reaction schemes 1 and 2, can be prepared analogously, or by using customary methods known per se to a person skilled in the art.

Reaction scheme 1:

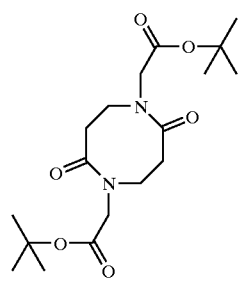
1. CH$_2$Cl$_2$/TFA
2. HCl/Et$_2$O
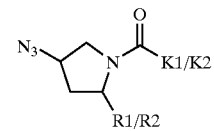
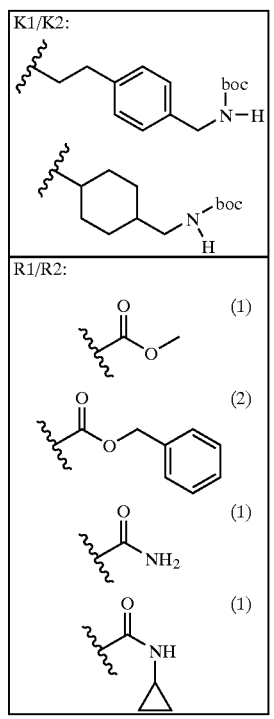
(1) MeOH
   PdC 10%
   H$_2$
   or
(2) Staudinger red
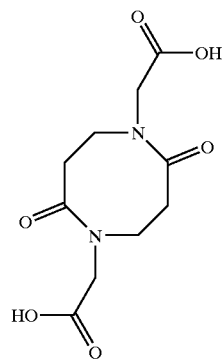
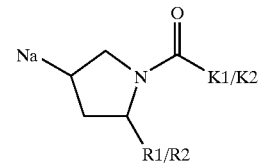
HBTU
DMF
Et$_3$N -continued
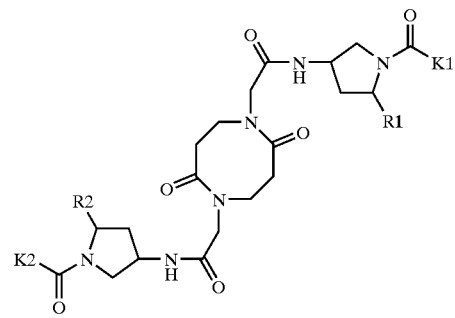
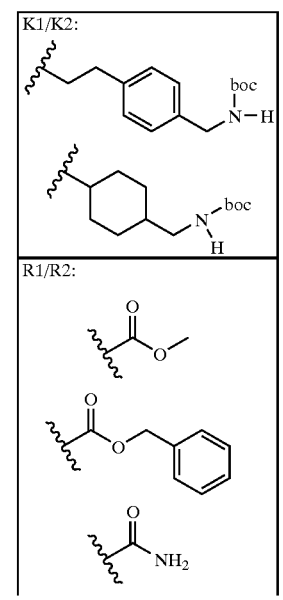
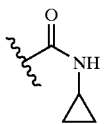
Reaction scheme 2:
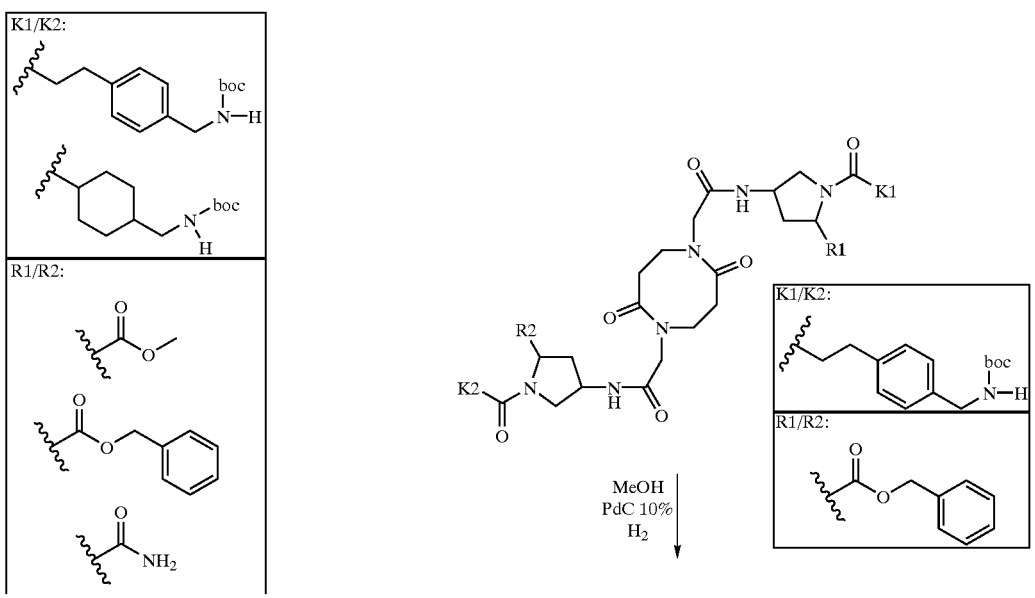

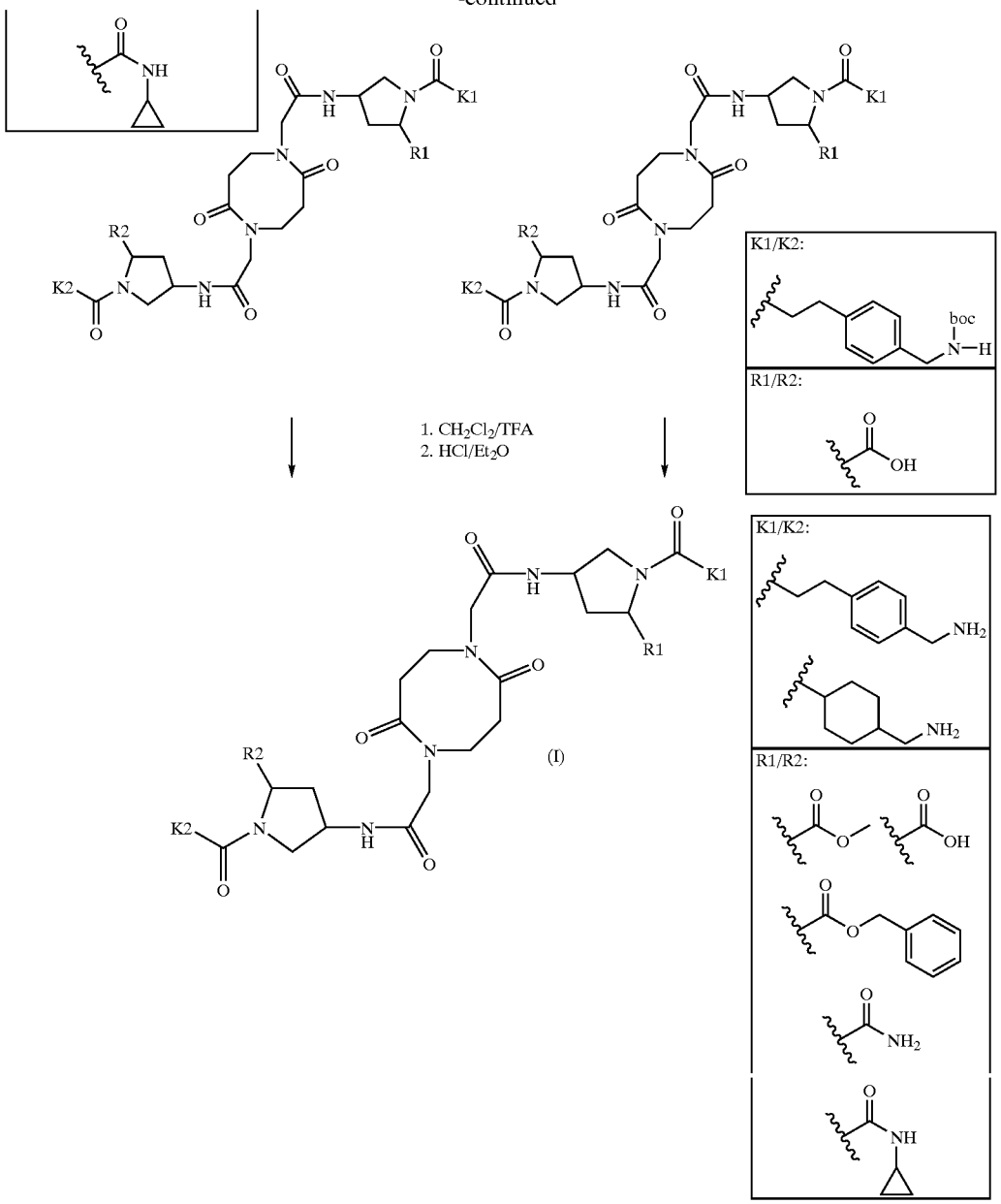

It is furthermore possible to convert compounds of the formula I by derivatization into other compounds of the formula I. Thus, for example, compounds of the formula I in which R6 and R7 are hydrogen can be converted by an alkylation reaction into compounds of the formula I in which R6 and R7 are 1–2C-alkyl. The person skilled in the art is familiar with suitable alkylation methods.

It is furthermore known to the person skilled in the art that if there are a number of reactive centers on a starting material or intermediate, it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent under reduced pressure and recrystallizing the resulting residue from a suitable solvent or subjecting it to one of the customary purification methods, such as, for example, column chromatography on a suitable stationary phase.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

In the examples below, the abbreviation RT denotes room temperature, h denotes hours, min denotes minutes, HBTU denotes O-(benzotriazol-1-yl)-N,N,N',N'-tetramethyluronium hexafluorophosphate and TOTU denotes O-[(ethoxycarbonyl)cyanomethyleneamino]-N,N,N',N'-tetramethyluronlum tetrafluoroborate.

The compounds mentioned by way of example and their salts are the preferred subject of the invention

EXAMPLES

End Products:

1. 1,5-Bis{N,N'-[1-(3-(4-aminomethylphenyl)propionyl)-2-methoxycarbonylpyrrolidin-4-yl]aminocarbonylmethyl}perhydro-1,5-diazocine-2,6-dione dihydrochloride

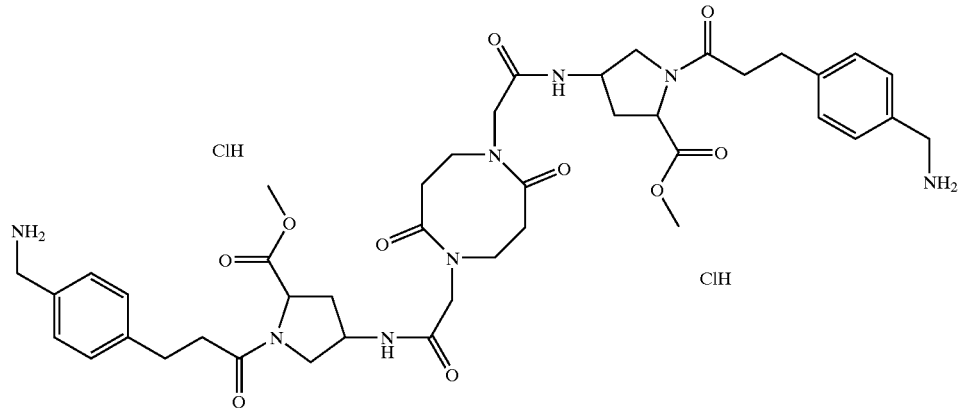

0.27 g of 1,5-bis-{N,N'-[1-(3-(4-tert-butyloxycarbonylaminomethylphenyl)propionyl)-2-methoxy-carbonylpyrrolidin-4-yl]aminocarbonylmethyl}perhydro-1,5-diazocine-2,6-dione (starting material A1) is dissolved in 2 ml of dichloromethane, and 2 ml of trifluoroacetic acid are then added. The mixture is stirred at RT for 2 hours, and 5 ml of a 2N solution of HCl in ether are then added. Following dilution with a further 15 ml of ether, the mixture is filtered off with suction under nitrogen and the solid is dried under high vacuum. This gives 0.22 g of the title compound; the mass spectrum shows the molecular peak MH$^+$ at 833 Da.

2. 1,5-Bis{N,N'-[1-(3-(4-aminomethylphenyl)propionyl)-2-benzyloxycarbonylpyrrolidin-4-yl]aminocarbonylmethyl}perhydro-1,5-diazocine-2,6-dione dihydrochloride

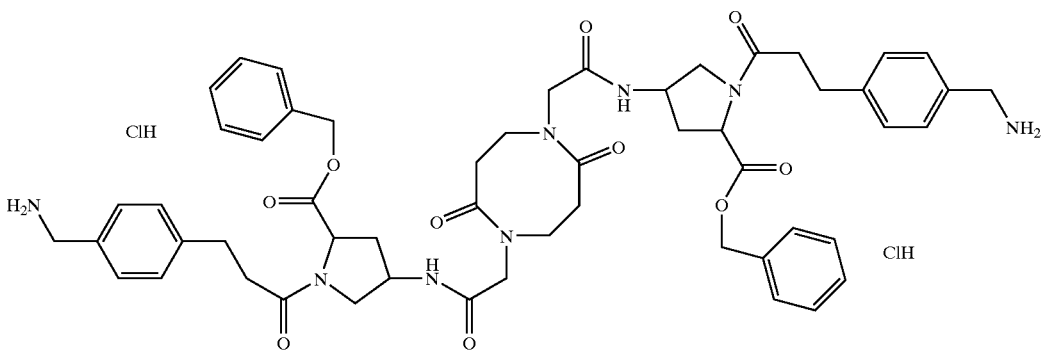

0.1 g of 1,5-bis-{N,N'-[1-(3-(4-tert-butyloxycarbonylaminomethylphenyl)propionyl)-2-benzyloxy-carbonylpyrrolidin-4-yl]aminocarbonylmethyl}perhydro-1,5-diazocine-2,6-dione (starting material B1) is dissolved in 1 ml of dichloromethane, and 1 ml of trifluoroacetic acid is then added. The mixture is stirred at RT overnight, 1 ml of a 2N solution of HCl in ether is then added, after 30 min, the mixture is diluted with about 20 ml of ether and the precipitate is filtered off with suction, washed with ether and dried under high vacuum. This gives 0.07 g of the title compound as a colorless powder; the mass spectrum shows the molecular peak $MH^+$ at 985 Da.

3. 1,5-Bis{N,N'-[1-(3-(4-aminomethylphenyl)proplonyl)-2-carboxypyrrlidin-4-yl]-aminocarbonylmethyl}perhydro-1,5-diazocine-2,6-dine dihydrochloride

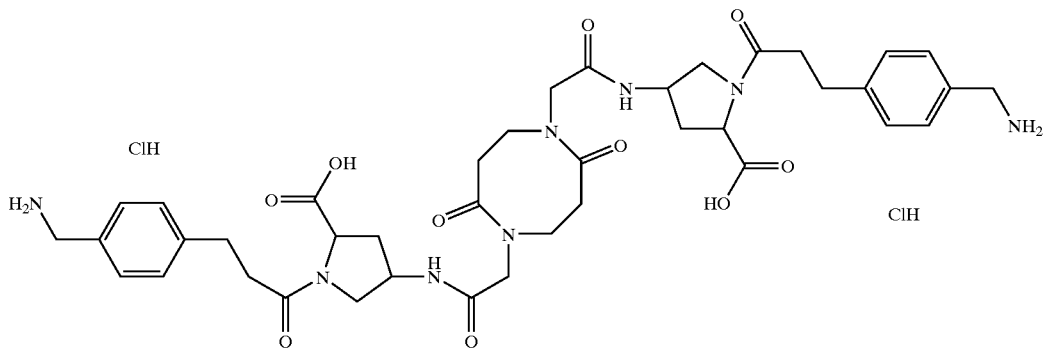

Analogously to example 2, 0.2 g of 1,5bis-{N,N'-[1-(3-(4-tert-butyloxycarbonyl-aminomethylphenyl)-propionyl)2-carboxypyrrolidinyl]aminocarbonylmethyl}perhydro-1,5-diazocine-2,6-dione (starting material C1) gives 0.14 g of the title compound as a colorless powder. The mass spectrum shows the molecular peaks $M_2H^+$ and $MH^+$ at 805 and 403 Da, respectively.

4. 1,5-Bis{N,N'-[1-(3-(4-aminomethylphenyl)propionyl)-2-cyclopropylaminocarbonyl-pyrrolidin-4-yl]aminocarbonylmethyl}perhydro-1,5-diazocine-2,6-dione dihydrochloride

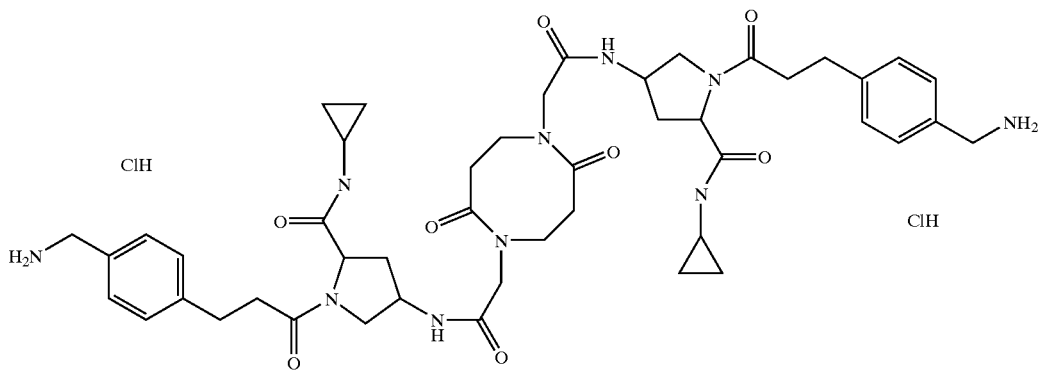

Analogously to example 2, 0.12 g of 1,5-bis{N,N'-[1-(3-(4-tert-butyloxycarbonylaminomethylphenyl)-propionyl)-2-cyclopropylaminocarbonylpyrrolidin-4-yl]aminocarbonylmethyl}-perhydro-1,5-diazocine-2,6-dione (starting material D1) gives 0.095 g of the title compound as a colorless powder. The mass spectrum shows the molecular peak $MH^+$ at 883 Da.

5. 1,5-Bis{N,N'-[1-(3-(4-aminomethylphenyl) proplonyl)-2-aminocarbonylpyrrolidin-4-yl]-aminocarbonylmethyl}perhydro-1,5-diazocine-2,6-dione dihydrochloride

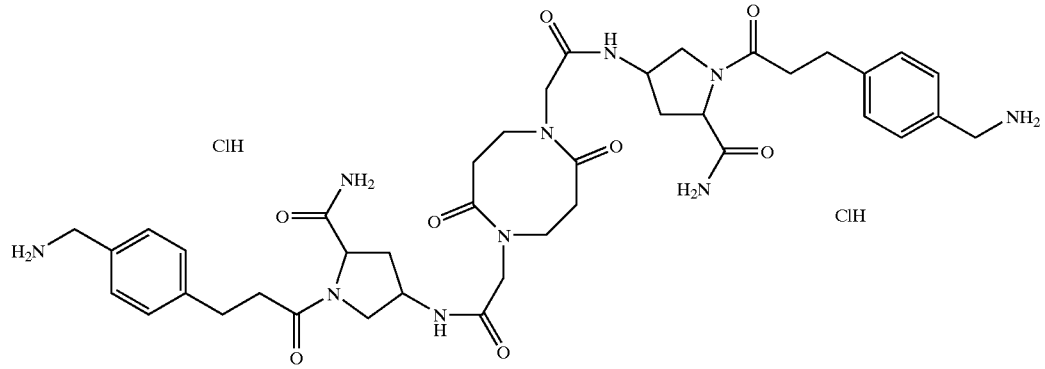

0.283 g of 1,5-bis-{N,N'-[1-(3-(4-tert-butyloxycarbonylaminomethylphenyl)propionyl)2-aminocarbonyl-pyrrolidin-4-yl]aminocarbonylmethyl}perhydro-1,5-diazocine-2,6-dione (starting material E1) gives, analogously to example 1, 0.25 g of the title compound as a virtually colorless powder. The mass spectrum shows the molecular peaks MH⁺ and MNa⁺ at 803 and 825 Da, respectively.

6. 1,5-Bis-{N,N'-[1-(4-aminomethylcyclohexanoyl)-2-methoxycarbonylpyrrolidin4-yl]-aminocarbonylmethyl}perhydro-1,5-diazocine-2,6-dione dihydrochloride

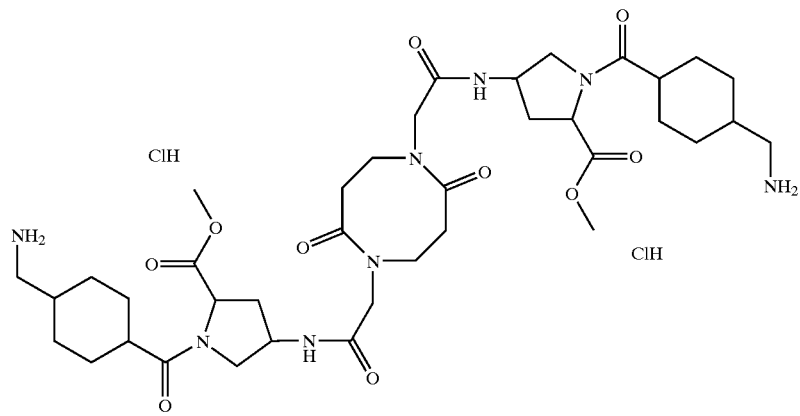

0.268 g of 1,5-bis{N,N'-[1-(4-tert-butyloxycarbonylaminomethylcyclohexanoyl)-2-methoxycarbonyl-pyrrolidin-4-yl]aminocarbonylmethyl}perhydro-1,5-diazocine-2,6-dione (starting material F1) gives, analogously to example 2, 0.214 g of the title compound as a colorless powder. The mass spectrum shows the molecular peak MH⁺ at 789 Da.

Starting Materials

A1. 1,5-Bis-{N,N'-[1-(3-(4-tert-butyloxycarb nylaminomethylphenyl)proplonyl)-2-meth xy-carbonylpyrrolidin-4-yl]aminocarbonylmethyl}perhydro-1,5-diazocine-2,6-dione With stirring, 0.236 g of (5-carboxymethyl-2,6-dioxoperhydro-1,5-diazocin-1-yl)acetic acid (starting material A2) and 0.755g of O-(benzotriazol-1-yl)-N,N,N',N'-tetramethyluroniumhexafluorophosphate (HBTU) are added successively to a solution of 0.380 ml of triethylamine in 5 ml of DMF. After 5 min, 0.741 g of methyl 4-amino-1-[3-(4-tert-butyloxycarbonylaminomethylphenyl)propionyl]prolinate (starting material A4) is added, and the mixture is stirred at RT overnight. The mixture is diluted with 10 ml of dichloromethane, water is added and the organic phase is, after phase separation, washed in each case once with 1N aqueous sodium hydroxide solution, 1N hydrochloric acid solution, saturated sodium bicarbonate solution and saturated sodium chloride solution. The organic phase is dried over magnesium sulfate and then concentrated, and the residue is chromatographed on a silica gel column (dichloromethane/methanol 98:2). Concentration of the chromatographically pure fractions and drying under high vacuum gives 0.3 g of the title compound as a colorless powder. The mass spectrum shows the molecular peaks MH⁺ and MNa⁺ at 1033 and 1055 Da, respectively.

A2. (5-Carboxymethyl-2,6-dioxoperhydro-1,5-diazocin-1-yl)acetic acid 1.4 g of tert-butyl (5-tert-butoxycarbonylmethyl-2,6-dioxoperhydro-1,5-diazocin-1-yl)acetate (starting material A3) are dissolved in 6 ml of dichloromethane, and 6 ml of trifluoroacetic acid are added. The mixture is stirred overnight and then concentrated using a rotary evaporator, and the residue is triturated with ethyl acetate/petroleum ether (1:1). The residue is filtered off with suction and dried under reduced pressure. This gives 0.89 g of the title compound which starts to melt at 250° C. (decomposition); the mass spectrum shows the molecular peaks MH⁺ and MNH₄⁺ at 259 and 276 Da, respectively.

A3. tert-Butyl (5-tert-butoxycarbonylmethyl-2,6-dioxoperhydro-1,5-diazocin-1-yl)acetate 3.3 g of perhydro-1,5-diazocine-2,6-dione are suspended in 30 ml of absolute DMF, and 732 mg of sodium hydride (80%) are then added. The mixture is stirred at RT for 15 min and then cooled to 0° C., and 3.76 ml of tert-butyl bromoacetate are then added. The mixture is stirred at 0° C. for 15 min and at RT for 30 min and then once more cooled to 0° C., and another 732 mg of sodium hydride (80%) are added. After 15 min, a further 3.76 ml of tert-butyl bromoacetate are added using a pipette, and after 15 min, the ice bath is removed and the mixture is stirred at RT overnight. The mixture is diluted with dichloromethane, water is added, the phases are separated and the organic phase is washed twice with water. The organic phase is dried over MgSO₄ and concentrated, and the residue is dried under high vacuum and recrystallized from n-hexane. This gives 2.5 g of the title compound of melting point 180° C.; the mass spectrum shows the molecular peaks MH⁺ and MNH₄⁺ at 371 and 388 Da, respectively.

A4. Methyl 4-amino-1-[3-(4-tert-butyloxycarbonylaminomethylphenyl)propionyl]prolinate 6.27 g of methyl 4-azido-1-[3-(4-tert-butyloxycarbonylaminomethylphenyl)propionyl]prolinate (starting material A5) are dissolved in 200 ml of methanol and, after addition of 0.6 g of Pd/C (10%), hydrogenated. After the reaction has ended, the catalyst is filtered off with suction and the filtrate is concentrated under reduced pressure. Drying under high vacuum gives 5.47 g of the title compound as a colorless solidified foam. The mass spectrum shows the molecular peak MH⁺ at 406 Da.

A5. Methyl 4-azido-1-[3-(4-tert-butyloxycarbonylaminomethylphenyl)proplonyl]prolinate 2.70 g of 3-(4-tert-butyloxycarbonylaminomethylphenyl)propionic acid (starting material A6) are dissolved in 40 ml of DMF, and 2.7 ml of triethylamine are added. The mixture is stirred for 5 min, and 3.63 g of HBTU and, after a further 5 min, 2 g of methyl (2S,4S)-4-azidoprolinate hydrochloride are added. The mixture is stirred at RT overnight, ethyl acetate and water are then added and the phases are separated. The organic phase is washed in each case once with 1N aqueous sodium hydroxide solution, 1N hydrochloric acid solution, saturated sodium bicarbonate solution and saturated sodium chloride solution. The organic phase is dried over magnesium sulfate and then concentrated and dried under high vacuum. This gives 4.1 g of the title compound as a light-orange oil. The mass spectrum shows the molecular peak MNH₄⁺ at 449 Da.

A6. 3-(4-tert-Butyloxycarbonylaminomethylphenyl) proplonic acid 4.65 g of methyl 3-(4-aminomethylphenyl)propionate hydrochloride (starting material A7) are dissolved in 20 ml of dichloromethane, and 6.17 ml of triethylamine and a solution of 4.62 g of di-tert-butyl dicarbonate in 10 ml of dichloromethane are added successively with stirring at 0° C. The reaction solution is stirred at 0° C. for 1 h and at RT for another 3 h and then washed twice with 0.1 N hydrochloric acid solution and then with sodium bicarbonate solution and water and dried over magnesium sulfate. The solution is filtered and then concentrated under reduced pressure and the residue (5.6 g) is dissolved in 50 ml of tetrahydrofuran, and 13.4 ml of 2N aqueous sodium hydroxide solution are added. The mixture is stirred at RT overnight and then neutralized with 6.7 ml of 4N hydrochloric acid solution, and the organic solvent is distilled off under reduced pressure. The resulting colorless precipitate is filtered off with suction, washed with water and dried under high vacuum. This gives 4.65 g of the title compound, the mass spectrum of which shows the molecular peak MNH₄⁺ at 297 Da.

A7. Methyl 3-(4-aminomethylphenyl)propionate hydrochloride 5.6 g of methyl 4-(hydroxyiminomethyl)cinnamate (starting material A8) are dissolved in a mixture of 170 ml of methanol and 50 ml of acetic acid and hydrogenated over 0.5 9 of palladium/carbon (10%) for 4 h. The catalyst is filtered off and the filtrate is concentrated under reduced pressure. The residue is stirred with ether, and a solution of hydrogen chloride in ether is then added. The resulting precipitate is filtered off with suction, washed with ether and dried under reduced pressure. This gives 4.65 g of the title compound. The mass spectrum shows the molecular peak MH⁺ at 194 Da.

A8. Methyl 4-(hydroxyiminomethyl)cinnamate 4.0 g of methyl 4-formylcinnamate are dissolved in 40 ml of methanol, and 1.6 g of hydroxylamine hydrochloride and 1.9 g of sodium acetate are then added successively. The mixture is stirred overnight and then diluted with 300 ml of water, and the resulting precipitate is filtered off with suction. Drying under high vacuum and recrystallization from ethyl acetate/petroleum ether gives 3.56 g of the title compound. The mass spectrum shows the molecular peak MH⁺ at 206 Da.

B1. 1,5-Bis-{N,N'-[1-(3-(4-tert-butyloxycarbonylaminomethylphenyl)propionyl)-2-benzyloxy-carbonyl-pyrrolidin-4-yl]-aminocarbonylmethyl}-perhydro-1,5-diazocine-2,6-dione Analogously to example A1, 0.54 g of (5-carboxymethyl-2,6-dioxoperhydro-1,5-diazocin-1-yl)acetic acid (starting material A2), 1.07 ml of diisopropylethylamine, 1.66 g of HBTU and 2.11 g of benzyl 4-amino-1-[3-(4-tert-butyloxycarbonylaminomethylphenyl)propionyl]prolinate (starting material B2) in 10 ml of DMF give, after column chromatography (silica gel; dichloromethane/methanol 98:2), 1.26 g of the title compound as a colorless powder. The mass spectrum shows the molecular peaks MH⁺, MNH₄⁺ and MNa⁺ at 1 185, 1 202 and 1 207 Da, respectively.

B2. Benzyl 4-amino-1-[3-(4-tert-butyloxycarbonylaminomethylphenyl)propionyl]prolinate 6.2 g of benzyl 4-azido-1-[3-(4-tert-butyloxycarbonylaminomethylphenyl)propionyl]prolinate (starting material B3) are dissolved in 50 ml of tetrahydrofuran, and 3.52 g of triphenylphosphine are then added a little at a time, as a result of which a clear evolution of gas can be observed. After 4 h of stirring at RT, 10 ml of water are added, and the mixture is stirred at RT for 6 days. 12.5 ml of 1N hydrochloric acid solution are added, and the mixture is then extracted twice with ethyl acetate. Using 13 ml of 1N sodium hydroxide solution, the aqueous phase is made slightly alkaline, and the phase is then extracted three times with a mixture of ether/methanol (8:2). The extract is dried over magnesium sulfate and then concentrated, and the residue is dried under high vacuum. This gives 2.22 g of the title compound as a viscous oil. The mass spectrum shows the molecular peaks $MH^+$, $MNa^+$ and $M_2H^+$ at 482, 504 and 962 Da, respectively.

B3. Benzyl 4-azido-1-[3-(4-tert-butyloxycarbonylaminomethylphenyl)propionyl] prolinate Analogously to example A5, 3.95 g of 3-(4-tert-butyloxycarbonylaminomethylphenyl)propionic acid (starting material A6), 2.16 ml of triethylamine, 5.36 g of HBTU and 3.48 g of benzyl (2S,4S)-4-azidoprolinate in 30 ml of DMF give 7.2 9 of the title compound. The mass spectrum shows the molecular peaks $MH^+$, $MNH_4^+$ and $M_2H^+$ at 507, 524 and 1 014 Da, respectively.

C1. 1,5-Bis{N,N'-[1-(3-(4-tert-butyloxycarbonyl-aminomethylphenyl)propionyl)-2-carboxy-pyrrolidin-4-yl]-aminocarbonylmethyl}perhydro-1,5-diazocine-2,6-dione 0.98 9 of 1,5-bis{N,N'-[1-(3-(4-tert-butyloxycarbonylaminomethylphenyl)proplonyl)-2-benzyloxy-carbonyl-pyrrolidin4-yl]-aminocarbonylmethyl}perhydro-1,5-diazocine-2,6-dione (starting material B1) in 30 ml of methanol is hydrogenated over 0.1 g of Pd/C (10%). After the reaction has ended, the catalyst is filtered off, the filtrate is evaporated to dryness and the residue is crystallized with ether. The crystals are filtered off with suction, washed with ether and dried under reduced pressure. This gives 0.79 g of the title compound as a colorless powder. The mass spectrum shows the molecular peaks $MH^+$, $MNH_4^+$ and $MNa^+$ at 1 005, 1 022 and 1 027 Da, respectively.

D1. 1,5-Bis{N,N'-[1-(3-(4-tert-butyloxycarbonyl-aminomethylphenyl)propionyl)-2-cyclo-propylaminocarbonyl-pyrrolidin-4-yl]-amino-carbonylmethyl}perhydro-1,5-diazocine-2,6-dione Analogously to example A1, 0.15 g of (5-carboxymethyl-2,6-dioxoperhydro-1,5-diazocin-1-yl)acetic acid (starting material A2), 0.2ml of triethylamine, 0.3249 of HBTU and 0.59 of 4-amino-1-[3-(4-tebutyloxycarbonylaminomethylphenyl)proplonyl] prolinecyclopropylamide (starting material D2) in 2 ml of DMF give, after column chromatography (silica gel; dichloromethane/methanol 9:1), 0.135 g of the title compound as a colorless powder. The mass spectrum shows the molecular peaks $MH^+$ and $MNa^+$ at 1 083 and 1 105 Da, respectively.

D2. 4-Amino-1-[3-(4-tert-butyloxycarbonylaminomethylphenyl)pr pionyllprolinecycl -propylamide Analogously to example A4, hydrogenation of 1.8 g of 4-azido-1-[3-(4-tert-butyloxy-carbonylamino-methylphenyl)propionyl]prolinecyclopropylamide (starting material D3) over 0.2 9 of Pd/C (10%) in 20 ml of methanol gives 1.5 9 of the title compound.

D3. 4-Azido-1-[3-(4-tert-butyloxycarbonylaminomethylphenyl) propionyllprolinecyclo-propylamide Analogously to example A5, 1.0 g of 3-(4-tert-butyloxycarbonylaminomethylphenyl)propionic acid (starting material A6), 1.5 ml of triethylamine, 1.64 g of HBTU and 1.21 g of (2S,4S)4-azidoproline-cyclopropylamide in 10 ml of DMF give 1.94 g of the HBTU compound. The mass spectrum shows the molecular peaks $MH^+$ and $MNa^+$ at 457 and 479 Da, respectively.

E1. 1,5-Bis{N,N'-(1-(3-(4-tert-butyloxycarbonyl-aminomethylphenyl)propionyl)-2-amino-carbonyl-pyrrolidin-4-yl]-aminocarbonylmethyl}perhydro-1,5-diazocine-2,6-dione Analogously to example A1, 0.277g of (5-carboxymethyl-2,6-dioxoperhydro-1,5-diazocin-1-yl)acetic acid (starting material A2), 0.34 ml of triethylamine, 0.814 g of HBTU and 0.84 g of 4-amino-1-[3-(4-tert-butyloxycarbonylaminomethylphenyl)propionyl] prolinamide (starting material E2) in 3 ml of DMF give, after column chromatography (silica gel; dichloromethane/methanol 85:15), 0.34 g of the title compound as a colorless powder. The mass spectrum shows the molecular peaks $MH^+$ and $MNa^+$ at 1 003 and 1 025 Da, respectively.

E2. 4-Amino-1-[3-(4-tert-butyloxycarbonylaminomethylphenyl)propionyl] prolinamide Analogously to example A4, hydrogenation of 1.05 g of 4-azido-1-[3-(4-tert-butyloxycarbonyl-aminomethylphenyl) propionyl]prolinamide (starting material E3) over 0.1 g of Pd/C (10%) in 20 ml of methanol gives 0.92 g of the title compound. The mass spectrum shows the molecular peak $MH^+$ at 391 Da.

E3. 4-Azido-1-[3-(4-tert-butyloxy-carbonylaminomethylphenyl)propionyl]prolinamide 1.73 g of 4-azido-1-[3-(4-tert-butyloxycarbonylaminomethylphenyl)propionyl]proline (starting material E4) are dissolved in 20 ml of DMF, and 0.86 ml of triethylamine and 1.36 g of TOTU (O-[(ethoxycarbonyl)cyanomethyleneamino]-N,N,N',N'-tetramethyluronium tetrafluoroborate) are then added successively with stirring. After 10 minutes, 8.3 ml of a solution of $NH_3$ in methanol (2M) are added, and the mixture is stirred at RT for 1 h. The mixture is then diluted with ethyl acetate, water is added and the phases are separated. The organic phase is washed in each case once with 1N aqueous sodium hydroxide solution, 1N hydrochloric acid solution, saturated sodium bicarbonate solution and saturated sodium chloride solution. The-organic phase is dried over magnesium sulfate and the residue is then chromatographed on a silica gel column (toluene/acetone 1:1). Concentration of the chromatographically pure fractions and drying under high vacuum gives 1.15 9 of the title compound as a colorless solidified foam. The mass spectrum shows the molecular peaks $MH^+$ and $MNH_4^+$ at 417 and 434 Da, respectively. 2.09 g of methyl 4-azido-1-[3-(4-tert-butyloxycarbonylaminomethylphenyl)proplonyl]prolinate (starting material A5) are dissolved in 20 ml of tetrahydrofuran, and 5.81 ml of a 1N NaOH solution are then added. The mixture is stirred overnight, 5.81 ml of a 1N HCl solution are added and the mixture is then diluted with about 30 ml of water and extracted three times with ethyl acetate. The organic phase is washed once with water, dried over $MgSO_4$ and then evaporated to dryness. This gives 1.84 g of the title compound as a colorless solidified foam. The mass spectrum shows the molecular peaks $MH^+$ and $MNa^+$ at 418 and 440 Da, respectively.

F. 1,5-Bis-{N,N'-[1-(4-tert-butyloxycarbonylaminomethyl-cyclohexanoyl)-2-methoxycarbonyl-pyrrolidin-4-yl]-aminocarbonylmethyl}perhydro-1,5-diazocine-2,6-dione Analogously to example A1, 0.1739 of (5-carboxymethyl-2,6-dioxoperhydro-1,5-diazocin-1-yl)acetic acid (starting material A2), 0.34ml of diisopropylethylamine, 0.539 of HBTU and 0.5159 of methyl 4-amino-1-(4-tert-butyloxycarbonylaminomethylcyclohexanoyl)prolinate (starting material F2) in 5 ml of DMF give, after column chromatography (silica gel; dichloromethane/methanol 94:6), 0.42 9 of the title compound as a colorless powder. The mass spectrum shows the molecular peaks $MH^+$ and $MNa^+$ at 989 and 1 011 Da, respectively.

F2. Methyl 4-amino-1-(4-tert-butyloxycarbonylaminomethyl-cyclohexanoyl)prolinate Analogously to example A4, hydrogenation of 5.0 9 of methyl 4-azido-1-(4-tert-butyloxycarbonylamino-methylcyclohexanoyl)prolinate (starting material F3) over 0.4 g of Pd/C (10%) in 160 ml of methanol gives 4.17 g of the title compound as a virtually colorless powder. The mass spectrum shows the molecular peak $MH^+$ at 384 Da.

F3. Methyl 4-azido-1-(4-tert-butyloxycarbonylaminomethylcyclohexanoyl)prolinate Analogously to example A5, 3.7 g of 4-tert-butyloxycarbonylaminomethylcyclohexanecarboxylic acid, 4.21 ml of triethylamine, 5.46 g of HBTU and 2.97 g of methyl (2S,4S)4-azidoprolinate hydrochloride in 70 ml of DMF give 5.03 g of the title compound. The mass spectrum shows the molecular peaks $MH^+$ and $MNa^+$ at 410 and 432 Da, respectively.

Commercial Utility

As tryptase Inhibitors, the compounds according to the invention have useful pharmacological properties which make them commercially utilizable. Human tryptase is a serin protease which is the main protein in human mast cells. Tryptase comprises eight closely related enzymes ($\alpha 1$, $\alpha 2$, $\beta 1a$, $\beta 1b$, $\beta 2$, $\beta 3$, mMCP-7-like-1, mMCP-7-like-2; 85 to 99% sequence Identity) (cf. Miller et al., J. Clin. Inves. 84 (1989) 1188–1195; Miller et al., J. Clin. Invest. 86 (1990) 864–870; Vanderslice et al., Proc. Natl. Acad. Sci., USA 87 (1990) 3811–3815; Pallaoro et al., J. Biol. Chem. 274 (1999) 3355–3362). However, only the $\beta$-tryptases (Schwartz et al., J. Clin. Invest. 96 (1995) 2702–2710; Sakai et al., J. Clin. Invest. 97 (1996) 988–995) are activated intracellularly and stored in catalytically active form in secretory granules. Compared with other known serin proteases, such as, for example, trypsin or chymotrypsin, tryptase has some special properties (Schwartz et al., Methods Enzymol. 244, (1994), 88–100; G. H. Caughey, "Mast cell proteases in immunology and biology". Marcel Dekker, Inc., New York, 1995). Tryptase from human tissue has a noncovalently-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly since an increased tryptase concentration was observed in a number of disorders of this type. Thus, tryptase is associated, inter alia, with the following diseases: acute and chronic (in particular inflammatory and allergen-induced) airway disorders of various origins (for example bronchitis, allergic bronchitis, bronchial asthma, COPD); interstitial lung disorders; disorders based on allergic reactions of the upper airways, (pharynx, nose) and the adjacent regions (for example paranasal sinuses, conjunctivae), such as, for example, allergic conjunctivitis and allergic rhinitis; disorders of the arthritis type (for example rheumatoid arthritis); autoimmune disorders, such as multiple sclerosis; furthermore neurogenic inflammations, arteriolosclerosis and cancer; moreover periodontitis, anaphylaxis, interstitial cystitis, dermatitis, psoriasis, sclerodermia/systemic sclerosis, inflammatory intestinal disorders (Crohn's disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of Tryptase in Allergic Inflammation" in: Protease Inhibitors, IBC Library Series, 1979, Chapter 3.3.1–3.3.23).

A further subject of the invention are the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by processes which are known per se and are familiar to the person skilled in the art; As medicaments, the compounds according to the invention (=active compounds) are either employed as such, or preferably in combination with suitable pharmaceutical excipients, for example in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of diseases of the respiratory tract, the compounds according to the invention are preferably also administered by inhalation, preferably in the form of an aerosol, with the aerosol particles of solid, liquid or mixed composition having a diameter of from 0.5 to 10 $\mu$m, advantageously of from 2 to 6 $\mu$m.

The aerosol can be produced, for example, using pressure-driven nozzle nebulizers or ultrasonic nebulizers, advantageously, however, using propellant gas-driven metered aerosols or by means of the propellant gas-free use of micronized active compounds from inhalation capsules.

Depending on the inhalation system employed, the administration forms also contain, in addition to the active compounds, the requisite auxiliary substances, for example propellant gases (e.g. Frigen in the case of metered aerosols), surface-active substances, emulsifiers, stabilizers, preservatives, aromatizing agents, fillers (e.g. lactose in the case of powder inhalers) and, where appropriate, additional active compounds.

For the purposes of inhalation, there are available a large number of appliances which can be used to generate aerosols of optimal particle size and administer them using an inhalation technique which is as appropriate as possible for the patient. In addition to using attachments (spacers and expanders) and pear-shaped containers (e.g. Nebulator® and Volumatic®), and also automatic spray puff releasers (Autohaler®) for metered aerosols, a number of technical solutions are available, particularly in the case of the powder inhalers (e.g. Diskhaler®, Rotadisk®, Turbohaler® or the inhaler described in European patent application 0 505 321), which technical solutions can be used to achieve optimal administration of the active compound.

For the treatment of dennatoses, the compounds according to the invention are in particular used in the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram per day.

Biological Investigations

The documented pathophysiological effects of mast cell tryptase are caused directly by the enzymatic activity of the protease. Accordingly, they are reduced or blocked by inhibitors which inhibit the enzymatic activity of the tryptase. A suitable measure for the affinity of a reversible inhibitor to the target protease is the equilibrium dissociation constant $K_1$ of the enzyme-inhibitor complex. This $K_1$ value can be determined via the effect of the inhibitor on the tryptase-induced cleavage of a chromogenic peptide-p-nitroanilide substrate or a fluorogenic peptide-aminomethylcoumarin substrate.

Methodology

The dissociation constants for the tryptase-inhibitor complexes are determined under equilibrium conditions in accordance with the general proposals of Bieth (Bieth J G, Pathophysiological Interpretation of kinetic constants of protease inhibitors, Bull. Europ. Physiopath. Resp. 16:183–195, 1980) and the methods of Sommerhoff et al. (Sommerhoff C P et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is isolated from lung tissue or prepared recombinantly; the specific activity of the protease, determined by titration, is usually greater than 85% of the theoretical value. In the presence of heparin (0.1–50 µg/ml) for stabilizing the protease, constant amounts of the tryptase are incubated with increasing amounts of the inhibitors. After an equilibrium between the reaction partners has formed, the remaining enzyme activity after addition of the peptide-p-nitroanilide substrate tos-Gly-Pro-arg-pNA is determined and the cleavage of the latter is monitored at 405 nm for 3 min. Alternatively, the remaining enzymatic activity can also be determined using fluorogenic substrates. The apparent dissociation constants $K_{Iapp}$ (i.e. in the presence of substrate) are subsequently determined by adapting the enzyme rates to the general equation for reversible inhibitors (Morrison J F, Kinetics of the reversible inhibition of enzyme-catalyzed reactions by tight-binding inhibitors, Biochim. Biophys. Acta 185, 269–286, 1969) using non-linear regression:

$$V_1/V_0 = 1 - \{E_t + I_t + K_{Iapp} - (E_t + I_t K_{Iapp})^2 - 4E_t I_t\}^{1/2}\}/2E_t$$

$V_1$ and $V_0$ are the rates in the presence and absence, respectively, of the inhibitor, and $E_t$ and $I_t$ are the tryptase and inhibitor concentrations, respectively.

The apparent dissociation constants determined for the compounds according to the invention are shown in Table A below, where the numbers of the compounds correspond to the numbers of the compounds in the examples [$pK_{Iapp}$=-log$K_{Iapp}$ (mol/l)].

TABLE A

| Inhibition of human tryptase | |
|---|---|
| Compound | $pK_{Iapp}$ |
| 1 | 9.05 |
| 2 | 9.22 |
| 3 | 7.43 |
| 4 | 9.66 |
| 5 | 8.80 |

What is claimed is:
1. A compound of the formula I

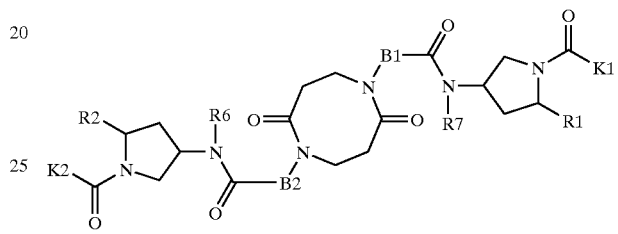

(I)

in which
K1 is —B3-Z1-B5-X1,
K2 is —B4-Z2-B6-X2,
B1 and B2 are identical or different and are 1–4C-alkylene,
B3 and B4 are identical or different and are a bond or 1–2C-alkylene,
B5 and B6 are identical or different and are a bond or 1–2C-alkylene,
X1 and X2 are Identical or different and are amino, aminocarbonyl, amidino or guanidino,
Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene,
R1 and R2 are identical or different and are C(O)OR3 or C(O)N(R4)R5,
R3 is hydrogen, 1–4C-alkyl, 3–7C-cycloalkyl, 3–7C-cycloalkylmethyl or benzyl,
R4 and R5 independently of one another are hydrogen, 1–4C-alkyl, 3–7C-cycloalkyl or 3–7C-cycloalkylmethyl, or R4 and R5 together, including the nitrogen atom to which they are attached, are a 1-pyrrolidinyl, 1-piperidinyl, 1-hexahydroazepinyl, 1-piperazinyl or 4-morpholinyl radical,
R6 and R7 are identical or different and are hydrogen or 1–2C-alkyl,
or a salt thereof.
2. A compound of the formula as claimed in claim 1, in which
K1 is —B3-Z1-B5-X1,
K2 is —B4-Z2-B6-X2,
B1 and B2 are identical or different and are 1–2C-alkylene,
B3 and B4 are identical or different and are a bond or 1–2C-alkylene, B5 and B6 are identical or different and are a bond or 1–2C-alkylene, X1 and X2 are identical or different and are amino or amidino, Z1 and Z2 are identical or different and are 1,3-phenylene, 1,4-phenylene, 1,3-cyclohexylene or 1,4-cyclohexylene, R1 and R2 are identical or different and are C(O)OR3 or C(O)N(R4)R5, R3 is hydrogen, 1–4C-alkyl, 3–7C-cycloalkyl, 3–7C-cycloalkylmethyl or benzyl, R4 and R5 independently of one another are hydrogen, 1–4C-alkyl, 3–7C-cycloalkyl or 3–7C-cycloalkylmethyl or R4 and R5 together, including the nitrogen atom to which they are attached, are a 1-pyrrolidinyl, 1-piperidinyl, 1-hexahydroazepinyl, 1-piperazinyl or 4-morpholinyl radical, R6 and R7 are identical or different and are hydrogen or 1–2C-alkyl, or a salt thereof.

3. A compound of the formula I as claimed in claim 1, in which

K1 is —B3-Z1-B5-X1,

K2 is —B4-Z-B6-X2,

B1 and B2 are identical or different and are 1–2C-alkylene,

B3 and B4 are identical or different and are a bond or 1–2C-alkylene,

B5 and B6 are identical or different and are a bond or 1–2C-alkylene,

X1 and X2 are identical or different and are amino or amidino,

Z1 and Z2 are identical or different and are 1,3-phenylene, 1,4-phenylene, 1,3-cyclohexylene or 1,4-cyclohexylene, R1 and R2 are identical or different and are C(O)OR3 or C(O)N(R4)R5, R3 is hydrogen, 1–4C-alkyl, 3–7C-cycloalkyl, 3–7C-cycloalkylmethyl or benzyl, R4 and R5 independently of one another are hydrogen, 1–4C-alkyl or 3–7C-cycloalkyl, R6 and R7 are identical and are hydrogen, or a salt thereof.

4. A compound of the formula I as claimed in claim 1, in which

K1 is —B3-Z1-B5-X1,

K2 is —B4-Z2-B6-X2,

B1 and B2 are identical and are methylene,

B3 and B4 are identical and are a bond or ethylene,

B5 and B6 are identical and are methylene,

X1 and X2 are identical and are amino,

Z1 and Z2 are identical and are 1,4-phenylene or 1,4-cyclohexylene,

R1 and R2 are identical and are C(O)OR3 or C(O)N(R4)R5,

R3 is hydrogen, 1–4C-alkyl or benzyl,

R4 is hydrogen,

R5 is hydrogen or cyclopropyl,

R6 and R7 are identical and are hydrogen, or a salt thereof.

5. A pharmaceutical composition comprising one or more compounds of the formula I as claimed in claim 1 or a pharmaceutically acceptable salt thereof together with a suitable pharmaceutical carrier and/or excipient.

6. A method of treating a disease or disorder in a patient comprising administering to a patient in need thereof a therapeutically effective amount of one or more compounds of the formula I as claimed in claim 1 or a pharmaceutically acceptable salt thereof, wherein the disease or disorder is selected from the group consisting of bronchitis, allergic bronchitis, bronchial asthma, COPD, allergic conjunctivitis, allergic rhinitis, rheumatoid arthritis, dermatitis, psoriasis, Crohn's disease and inflammatory bowel disease.

7. A method of treating a respiratory disorder in a patient comprising administering to a patient in need. thereof a therapeutically effective amount of one or more compounds of the formula I as claimed in claim 1 or a pharmaceutically acceptable salt thereof, wherein the respiratory disorder is selected from the group consisting of bronchitis, allergic bronchitis, bronchial asthma, COPD and allergic rhinitis.

* * * * *

UNITED STATES PATENT AND TRADEMARK OFFICE
CERTIFICATE OF CORRECTION

PATENT NO. : 6,924,305 B2
DATED : August 2, 2005
INVENTOR(S) : Ulrich

It is certified that error appears in the above-identified patent and that said Letters Patent is hereby corrected as shown below:

Column 24,
Line 39, please delete "Identical" and replace with -- identical --.

Column 25,
Line 28, please delete "-B4-Z-B6-X2" and replace with -- -B4-Z2-B6-X2 --.

Column 26,
Line 38, please delete "need. thereof" and replace with -- need thereof --.

Signed and Sealed this

Eleventh Day of October, 2005

JON W. DUDAS
*Director of the United States Patent and Trademark Office*